US00PP09572P

United States Patent [19]

Endisch et al.

[11] Patent Number: Plant 9,572

[45] Date of Patent: Jun. 4, 1996

[54] GERANIUM PLANT 'TOSSA'

[75] Inventors: Gerd Endisch, Geranienweg, D-76767, Hagenbach; Ursula Endisch-Burmeister, Bad Kreuznach, both of Germany; Wolf Endisch, Valle Guerra/Teneriffa, Spain

[73] Assignee: Gerd Endisch, Hagenbach, Germany

[21] Appl. No.: 384,159

[22] Filed: Feb. 6, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,350 10/1990 Craig ..... Plt./87.12

P.P. 8,287 6/1993 Trees ..... Plt./87.12

P.P. 8,552 1/1994 Trees ..... Plt./87.12

*Primary Examiner*—James R. Feyrer

*Attorney, Agent, or Firm*—Willian Brinks Hofer Gilson & Lione

[57] ABSTRACT

A new and distinct cultivar of geranium known by the cultivar name 'Tossa' is characterized by a light rose colored flower, a semi-double flower form, medium green foliage with medium zonation, medium flower response in springtime and a compact habit.

1 Drawing Sheet

BACKGROUND OF THE NEW PLANT

The present invention comprises a new and distinct cultivar of geranium botanically known as *Pelargonium zonale,* and hereinafter referred to by the cultivar name 'Tossa'. 'Tossa' is a product of planned breeding program which had the objective of creating new geranium cultivars with light rose flower color, semi-double flower form, and medium green foliage. 'Tossa' was orignated from a hybridization made in a controlled breeding program in Hagenbach, Germany, in 1991.

The female parent was 'Epos', characterized by its light pink flower color, with red markings, medium green foliage without zonation, semi-double flower form. 'Epos' was patented in Germany but is no longer commercially available. 'Tossa' differs from 'Epos' in terms of their respective flower characterizations as described above. Additionally, the leaves of 'Tossa' are zonated whereas the leaves of 'Epos' are not. The male parent of 'Tossa' was 'Laura', characterized by its pink flower color, semi-double flower form, light green foliage without zonation. 'Tossa' was discovered and selected as one flowering plant within the progeny of the stated cross by the named inventors in September 1992 in a controlled environment in Hagenbach, Germany.

DESCRIPTION OF THE NEW PLANT

The first act of asexual reproduction of 'Tossa' was accomplished when vegetative cuttings were taken from the initial selection in Jan. 1993 in a controlled environment in Hagenbach, Germany, by a technician working under formulations established and supervised by Gerd Endisch.

Horticultural examination of selected units initiated in May 1993 has demonstrated that the combination of characteristics as herein disclosed for 'Tossa' are firmly fixed and are retained through successive generations of asexual reproduction.

'Tossa' has not been observed under all possible environmental conditions. The phenotype may vary significantly with variations in environment such as temperature, light intensity, and day length. The following observations, measurements, and comparisons describe plants grown in Hagenbach, Germany, under field conditions which approximate those generally used in commercial practice. The measurements and dimensions given below are approximate.

The following traits have been repeatedly observed and are determined to be basic characteristics of 'Tossa' to distinguish this geranium as a new and distinct cultivar:

1. light rose flower color
2. semi-double flower form
3. medium green foliage with medium zonation
4. medium flower response in springtime
5. compact habit Of the many commercial cultivars known to the present inventor, the most similar in comparison to 'Tossa' is 'Goesta'. Reference is made to the Chart A below which compares certain characteristics of 'Tossa' to those same characteristics of 'Goesta'. In comparison to 'Goesta', 'Tossa' has a lighter color and a stronger zonation, bigger corolla, shorter peduncle and pedicle length and a more compact habit.

BRIEF DESCRIPTION OF THE DRAWINGS

The accompanying photographic drawing show typical flower and foliage characteristics of 'Tossa', with colors being as true as possible with illustrations of this type.

DETAILED BOTANICAL DESCRIPTION

In the following description color references are made to *The Royal Horticultural Society Colour Chart* (R.H.S.). The color values were determined indoors from plants grown outdoors in August 1994 in Hagenbach, Germany, or Hannover (Bundessortenamt).

Classification

*Botanical.*—A hybrid of the species *Pelargonium zonale.*

*Commercial.*—Zonal geranium, cv. 'Tossa'.

Inflorescence:

*Umbel.*—An umbel comprises approximately 28 flowers.

*Average diameter.*—Approx. 100 mm.

*Average depth.*—Approx. 45–50 mm.

*Peduncle length.*—Approx. 150–160 mm.

*Flower response.*—In Hannover, Germany, in 1993, 50% of plants with at least one flower opened 15 weeks after planting of unrooted cuttings; in Hannover (Bundessortenamt) medium, first flower 22 Apr. 1994.

*Outdoor flower production.*—In Haganbach, Germany, the flower count in 1993 indicated between 45–50 flowers per plant for May 15 through Aug. 15 observation period.

Corolla:

Blooming habit.—Continuous throughout the year, unit frost destroys plant.

*Average diameter.*—Approx. 44–48 mm.

*Form.*—Semi-double; cup shaped when bloom first opens, later flattening to shallow cup.

*Color.*—(General tonality from a distance of three meters) light rose.

*Petals.*—Number 6–8; approx. 21–23 mm across.

*Petal color (upper petals).*—R.H.S. 68 C (top surface), R.H.S. 65 C (bottom surface).

*Petal color (lower petals).*—R.H.S. 65 C (top surface); R.H.S. 65 DC (bottom surface); the base of the lower petals is crossed by a red colored strip of about 2 mm width.

*Color of the stripe.*—R.H.S. 65 A; the margin is white.

*Pedicel length.*—Approx. 26–30 mm.

*Pedicel color.*—Generally green, partially light red (anthocyanin) color.

*Petaloids.*—Normally 0 to 1 of various size.

Bud:

*Size.*—1.0–1.3 cm across.

*Shape.*—Elliptic.

*Color.*—Green.

*Sepals.*—Five to six in number; pointed linear lanceolate; at time of petal appearance, about 8 mm in length.

Reproductive organs:

*Stamens.*—Anthers: 6–8 in number. Filaments: Approx. 5–7 mm in length.

*Pollen: Orange in color.*

*Pistil.*—No.: One. Length: Approx. 9 mm.

*Stigma:* 7–8 lobes.

*Style: Approx.* 3 mm in length, color: red.

*Ovaries.*—Green.

*Fruit.*—Partially fertile.

*Durability.*—Medium rain resistance.

Plant:

*Foliage.*—Abundant quantity, leaves with zonation which ranges from the middle of the leaf to the edge. Form: Reniform in plan. Size: Approx. 8.5–10.0 cm across. Margin: Bicrenate. Texture: Smooth. Rib and veins: Distinct venation on the bottom side but not prominently different on the top surface. Color (upper surface): R.H.S. 137 AB; zone of upper surface: R.H.S. 137 A. Color (bottom surface): R.H.S. 137 D. Color (zonation): R.H.S. 137 C. Petioles: Approx. 9–10 cm in length, green.

*General appearance and form.*—Bushy and compact. Internode length: Approx. 18–20 mm. Branching pattern: Self-branching from base; in 1994, 18 branches observed Aug. 15. Height: Approx. 18–20 cm from media surface.

CHART A

| | New Cultivar Name: 'TOSSA' | Comparison Cultivar Name: 'Goesta' |
|---|---|---|
| Umbel depth | 45–50 | 50–55 mm |
| Penduncle length | 150–160 | 185 195 mm |
| Pedicel length | 26–30 | 30–34 mm |
| Internode length | 18–20 | 26–28 mm |

What is claimed is:

1. A new and distinct cultivar of geranium plant known as 'Tossa', as described and illustrated and particularly characterized by a light rose colored flower, a semi-double flower form, medium green foliage with medium zonation, medium flower response in springtime and a compact habit.

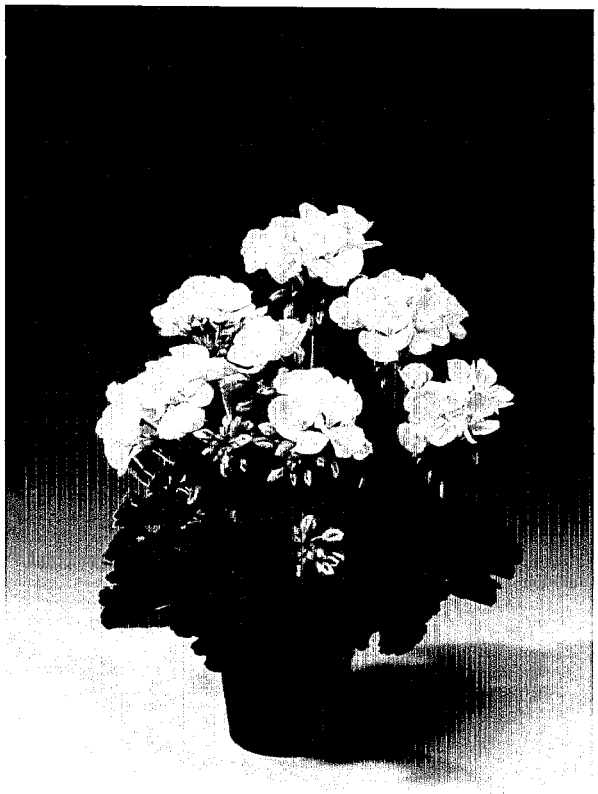

* * * * *